United States Patent
Zerkowski et al.

(10) Patent No.: US 11,510,781 B2
(45) Date of Patent: Nov. 29, 2022

(54) ANNULOPLASTY IMPLANT

(71) Applicant: Medtentia International Ltd Oy, Espoo (FI)

(72) Inventors: Hans-Reinhard Zerkowski, Kreuzlingen (CH); Olli Keränen, Bjärred (SE)

(*) Notice: Subject to any disclaimer, the term of this patent is extended or adjusted under 35 U.S.C. 154(b) by 0 days.

(21) Appl. No.: 16/615,722

(22) PCT Filed: May 22, 2018

(86) PCT No.: PCT/EP2018/063421
§ 371 (c)(1),
(2) Date: Nov. 21, 2019

(87) PCT Pub. No.: WO2018/215494
PCT Pub. Date: Nov. 29, 2018

(65) Prior Publication Data
US 2020/0205974 A1 Jul. 2, 2020

(30) Foreign Application Priority Data
May 23, 2017 (EP) .................................. 17172505

(51) Int. Cl.
*A61F 2/24* (2006.01)
(52) U.S. Cl.
CPC .......... *A61F 2/2445* (2013.01); *A61F 2/2463* (2013.01); *A61F 2230/0091* (2013.01); *A61F 2240/002* (2013.01)
(58) Field of Classification Search
CPC .... A61F 2/2409; A61F 2/2412; A61F 2/2418; A61F 2/2427; A61F 2/2445;
(Continued)

(56) References Cited

U.S. PATENT DOCUMENTS

| | | | |
|---|---|---|---|
| 11,246,707 B2 * | 2/2022 | Zerkowski | A61F 2/2445 |
| 2005/0079200 A1 | 4/2005 | Rathenow et al. | |

(Continued)

FOREIGN PATENT DOCUMENTS

| | | |
|---|---|---|
| CN | 203970617 U | 12/2014 |
| CN | 105748173 A | 7/2016 |

(Continued)

OTHER PUBLICATIONS

Translation of Chinese Patent CN203970617U Beijing Star Medical Devices Co. LTD dated Dec. 2014 (Year: 2014).*
Translation of Chinese Utility Model Patent Publication No. CN203970617U granted Dec. 3, 2014 to Beijing Star Medical Devices Co. Ltd. (Year: 2014).*
Espacenet Abstract of CN 105748173.
Espacenet Abstract of CN 203970617.
(Continued)

*Primary Examiner* — Paul B Prebilic
(74) *Attorney, Agent, or Firm* — Patent Grove LLC; Tomas Friend

(57) ABSTRACT

An annuloplasty implant is disclosed comprising first and second support rings arranged in a coiled configuration around an axial direction, and being adapted to be arranged on opposite sides of native heart valve leaflets to pinch said leaflets. At least part of said first and second support ring is formed from a carbon fiber material. The first and second support rings are resiliently movable with respect to each other in opposite directions along said axial direction. A method of manufacturing an annuloplasty implant is also disclosed.

9 Claims, 10 Drawing Sheets

(58) Field of Classification Search
CPC ............ A61F 2/2436; A61F 2210/0014; A61F 2210/0076; A61F 2220/0008; A61F 2230/0091; A61F 2230/0069; A61F 2250/0008; A61F 2250/006
See application file for complete search history.

(56) References Cited

U.S. PATENT DOCUMENTS

| | | | | |
|---|---|---|---|---|
| 2007/0191939 A1* | 8/2007 | Ryan | ............... | A61F 2/2442 623/2.36 |
| 2009/0177270 A1* | 7/2009 | Agnew | ............... | A61F 2/2418 623/1.24 |
| 2016/0199177 A1* | 7/2016 | Spence | ............... | A61F 2/2412 623/2.38 |
| 2022/0054262 A1* | 2/2022 | Spence | ............... | A61F 2/2436 |

FOREIGN PATENT DOCUMENTS

| | | | |
|---|---|---|---|
| WO | 2008071817 | A1 | 6/2008 |
| WO | 2016038017 | A1 | 3/2016 |

OTHER PUBLICATIONS

Espacenet Abstract of WO 2008071817.
International Search Report for International Application No. PCT/EP2018/063412, dated Jun. 21, 2018 (3 pages).
Espacenet Abstract of CN 105748173, (Jul. 2016).
Espacenet Abstract of CN 203970617, (Dec. 2014).
Espacenet Abstract of WO 2008071817, (Jun. 2008).

* cited by examiner

ANNULOPLASTY IMPLANT

CROSS-REFERENCE TO RELATED APPLICATIONS

This application claims priority to International Application No. PCT/EP2018/063421, filed May 22, 2018 and titled "ANNULOPLASTY IMPLANT," which in turn claims priority from a European Patent Application having application number 17172505.4, filed May 23, 2017, titled "ANNULOPLASTY IMPLANT," both of which are incorporated herein by reference in their entireties.

FIELD OF THE INVENTION

This invention pertains in general to the field of cardiac valve replacement and repair. More particularly the invention relates to an annuloplasty implant, such as an annuloplasty ring or helix, for positioning at the heart valve annulus and a method of manufacturing an annuloplasty implant.

BACKGROUND OF THE INVENTION

Diseased mitral and tricuspid valves frequently need replacement or repair. The mitral and tricuspid valve leaflets or supporting chordae may degenerate and weaken or the annulus may dilate leading to valve leak. Mitral and tricuspid valve replacement and repair are frequently performed with aid of an annuloplasty ring, used to reduce the diameter of the annulus, or modify the geometry of the annulus in any other way, or aid as a generally supporting structure during the valve replacement or repair procedure.

A problem with prior art annuloplasty implants lack of flexibility of the implant in certain situations, which impedes optimal functioning when implanted in the moving heart, or adaptability to varying anatomies. While the elastic properties are important, an annuloplasty implant is also intended to function for years and years, so it is critical with long term stability. Material fatigue may nevertheless lead to rupture of the material, which may be unexpected and uncontrolled. This entails a higher risk to the patient and it is thus a further problem of prior art devices.

A further problem with prior art annuloplasty implants is the complex manufacturing thereof. Annuloplasty implants may have to be manufactured by time-consuming milling processes. Such manufacturing processes may also impede patient specific tailoring of the implants. The annuloplasty implants are thus cumbersome to optimize to the anatomy of the specific patient. This entails a higher risk to the patient and is thus a further problem of prior art devices.

The above problems may have dire consequences for the patient and the health care system. Patient risk is increased.

Hence, an improved annuloplasty implant would be advantageous and in particular allowing for avoiding more of the above mentioned problems and compromises, and in particular allowing for improved accommodation to the valve anatomy, secure long-term functioning, and facilitated manufacturing and tailoring of the annuloplasty implant to varying anatomies. A related manufacturing method would also be advantageous.

SUMMARY OF THE INVENTION

Accordingly, examples of the present invention preferably seek to mitigate, alleviate or eliminate one or more deficiencies, disadvantages or issues in the art, such as the above-identified, singly or in any combination by providing a device according to the appended patent claims.

According to a first aspect an annuloplasty implant is provided comprising first and second support rings arranged in a coiled configuration around an axial direction, and being adapted to be arranged on opposite sides of native heart valve leaflets to pinch said leaflets. At least part of said first and second support ring is formed from a carbon fiber material. The first and second support rings are resiliently movable with respect to each other in opposite directions along said axial direction.

According to a second aspect a method of manufacturing an annuloplasty implant is provided comprising forming first and second support rings arranged in a coiled configuration around an axial direction, and forming at least part of said first and second support ring from a carbon fiber material.

According to a third aspect a method of manufacturing an annuloplasty implant is provided comprising determining dimensions of an annuloplasty implant based on a three-dimensional reconstruction of a heart valve determined from patient medical imaging data, forming first and second support rings arranged in a coiled configuration around an axial direction by three-dimensional printing for patient-specific manufacturing of the annuloplasty implant according to said dimensions, wherein at least part of said first and second support ring is formed by depositing a carbon fiber material in a layer by layer deposition by said three-dimensional printing.

Further examples of the invention are defined in the dependent claims, wherein features for the second and subsequent aspects are as for the first aspect mutatis mutandis.

Some examples of the disclosure provide for increased safety in case of material fatigue and rupture.

Some examples of the disclosure provide for securing long-term functioning and position of an annuloplasty implant.

Some examples of the disclosure provide for a more flexible implant.

Some examples of the disclosure provide for improved accommodation of an annuloplasty implant to varying anatomies.

Some examples of the disclosure provide for facilitated tailoring of an annuloplasty implant to patient specific anatomies.

Some examples of the disclosure provide for facilitated manufacturing of an annuloplasty implant.

Some examples of the disclosure provide for a less costly manufacturing of an annuloplasty implant.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DESCRIPTION OF EMBODIMENTS

Figure 1:
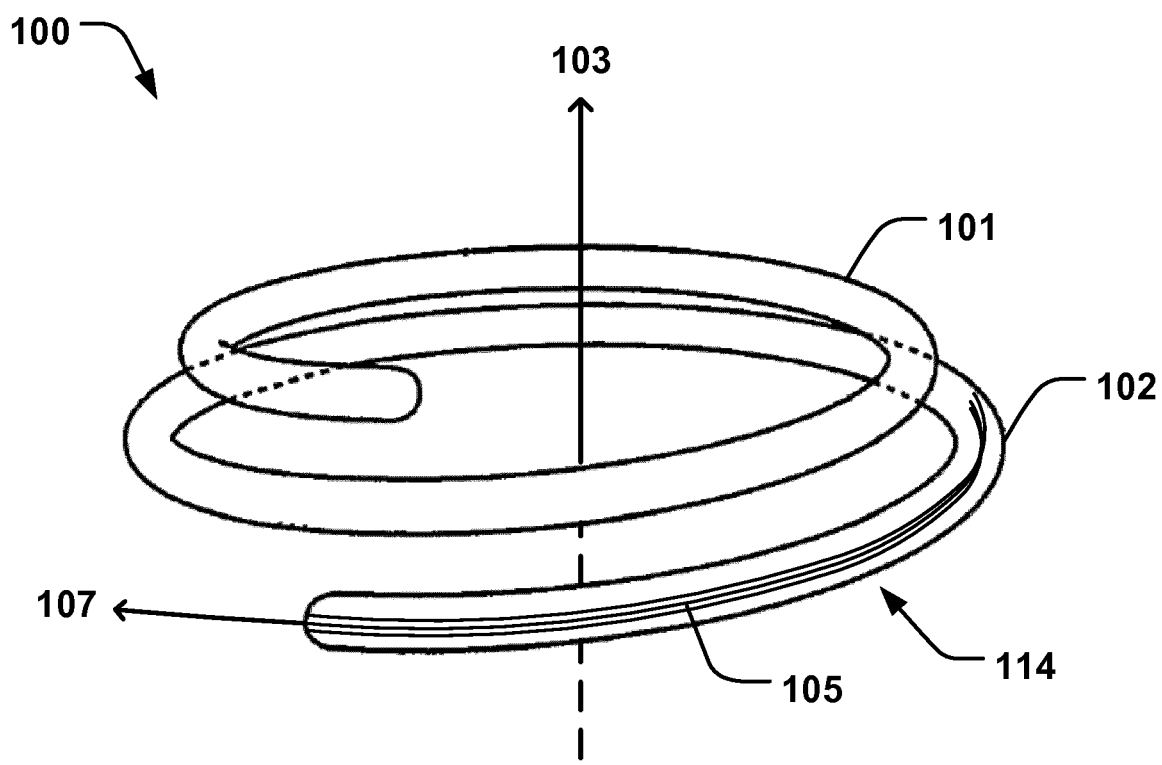
FIG. 1 is a schematic illustration of an annuloplasty implant according to one example.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

The following description focuses on an embodiment of the present invention applicable to cardiac valve implants such as annuloplasty rings. However, it will be appreciated that the invention is not limited to this application but may be applied to many other annuloplasty implants and cardiac valve implants including for example replacement valves, and other medical implantable devices.

Figure 2:
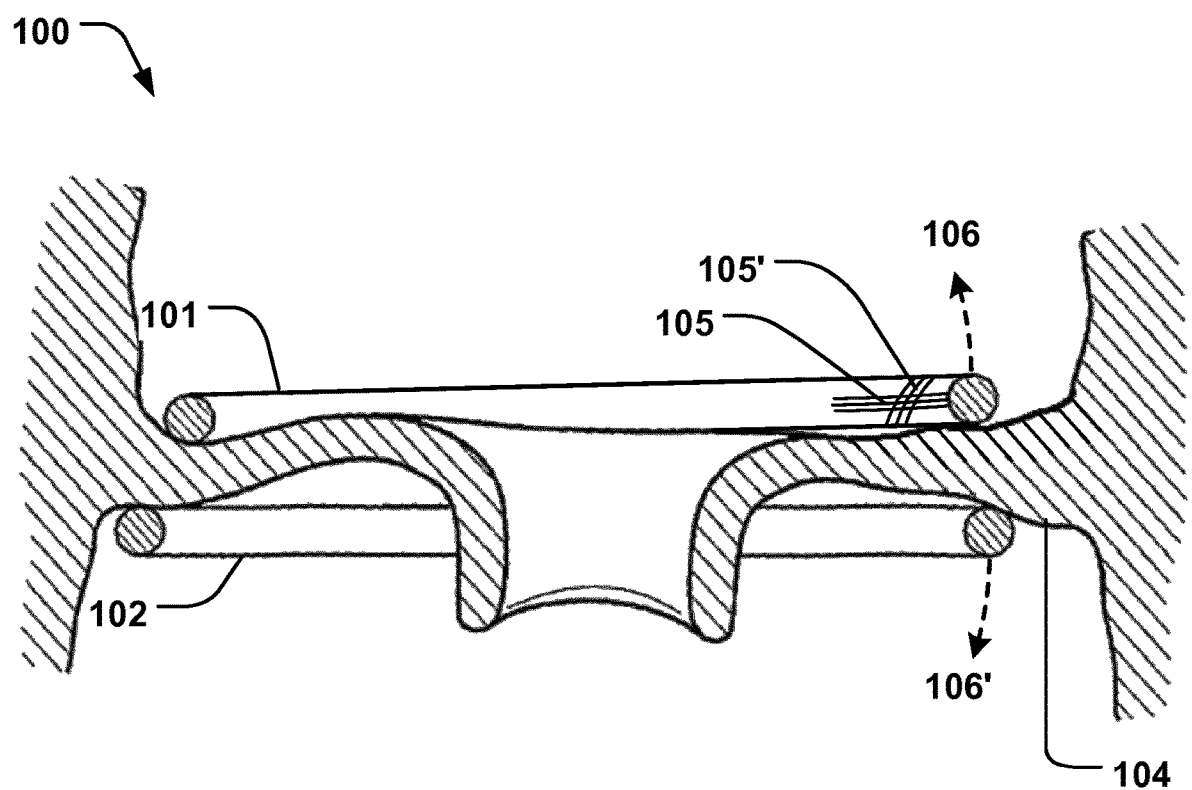
FIG. 2 is a schematic illustration of an annuloplasty implant according to one example, positioned at a heart valve.

FIG. 1 schematically illustrates an annuloplasty implant 100 comprising a first support ring 101 and a second support ring 102, being arranged in a coiled configuration around an axial direction 103. The first and second support rings 101 and 102 are adapted to be arranged on opposite sides of native heart valve leaflets 104 to pinch said leaflets. FIG. 2 illustrates the first and second support rings 101 and 102 arranged on each side of the valve leaflets 104. At least part of the first and second support rings 101 and 102 is formed from a carbon fiber material 105. The first and second support rings 101 and 102 are resiliently movable with respect to each other in opposite directions 106, 106', along said axial direction 103, as illustrated in FIG. 2. Having at least part of the first and second support rings 101 and 102 formed from a carbon fiber material 105 provides for advantageous flexible characteristics between the first and second support rings 101 and 102 in directions 106 and 106', that allows for securely pinching the tissue between the rings 101 and 102 for secure fixation thereof, while being sufficiently flexible to accommodate to movements of the beating heart as required, and thereby minimizing harmful interference with the surrounding tissue. Long term functioning may thus be improved, with a minimized risk of damage to the tissue or the annuloplasty implant 100 itself. Having at least part of the first and second support rings 101 and 102 formed from a carbon fiber material 105 also provides for an annuloplasty implant 100 of reduced weight, and thereby reduced inertia, which allows for improved accommodation to the dynamics of the movement of the surrounding tissue, with reduced forces exerted on the valve and the heart as a consequence. In addition to minimizing harmful interference with the heart, the reduced weight will also facilitate secure fixation of the annuloplasty implant 100 to the heart valve, due to the reduced forces associated with the movement of the annuloplasty implant 100 when fixated to the valve. Having a coil- or helix-shaped annuloplasty implant 100 formed at least part from a carbon fiber material 105 thus provides for particularly synergistic effects in providing a secure fixation—via improved pinching effect and reduced weight—and improved dynamical accommodation and long-term stability in the heart. It is conceivable that the carbon fiber material 105, 105, may have shape-memory properties, such that the first and second support rings 101 and 102 may assume an elongated configuration when delivered in a catheter, whereupon the first and second support rings 101 and 102 may assume the coiled configuration when ejected from the delivery catheter.

The carbon fiber material 105 may comprise a first plurality carbon fibers 105 extending substantially in a longitudinal direction 107 of the first and/or second support rings 101 and 102 along an annular periphery 114 thereof, as schematically illustrated in FIG. 1. The first and second support rings 101 and 102 are adapted to be resiliently movable in perpendicular directions to the longitudinal direction 107 of the carbon fibers 105. I.e. the carbon fibers 105 may flex in transverse directions to the longitudinal direction 107. Having the carbon fibers 105 extending in the longitudinal direction 107 may thus further improve the elastic and flexible characteristics of the annuloplasty implant 100 in e.g. the opposite directions 106, 106', along the axial direction 103, being substantially perpendicular to the longitudinal direction 107. The first plurality carbon fibers 105 may extend substantially in the longitudinal direction 107 of both the first and second support rings 101 and 102 or only one of the first and second support rings 101 and 102. The former case may provide for improved characteristics with the advantages as discussed above.

Figure 3:
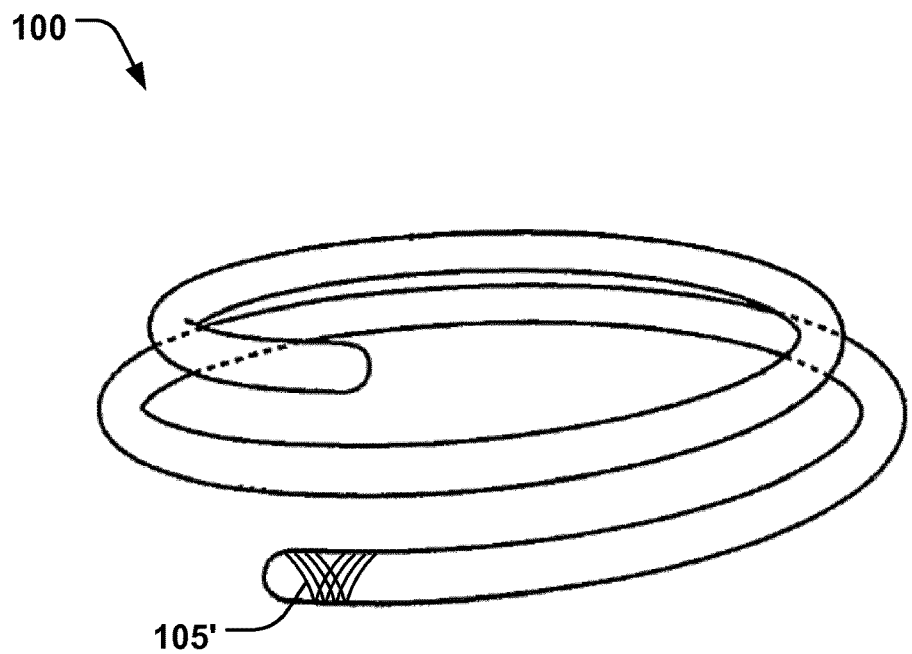
FIG. 3 is a schematic illustration of an annuloplasty implant according to one example.
Figure 4:
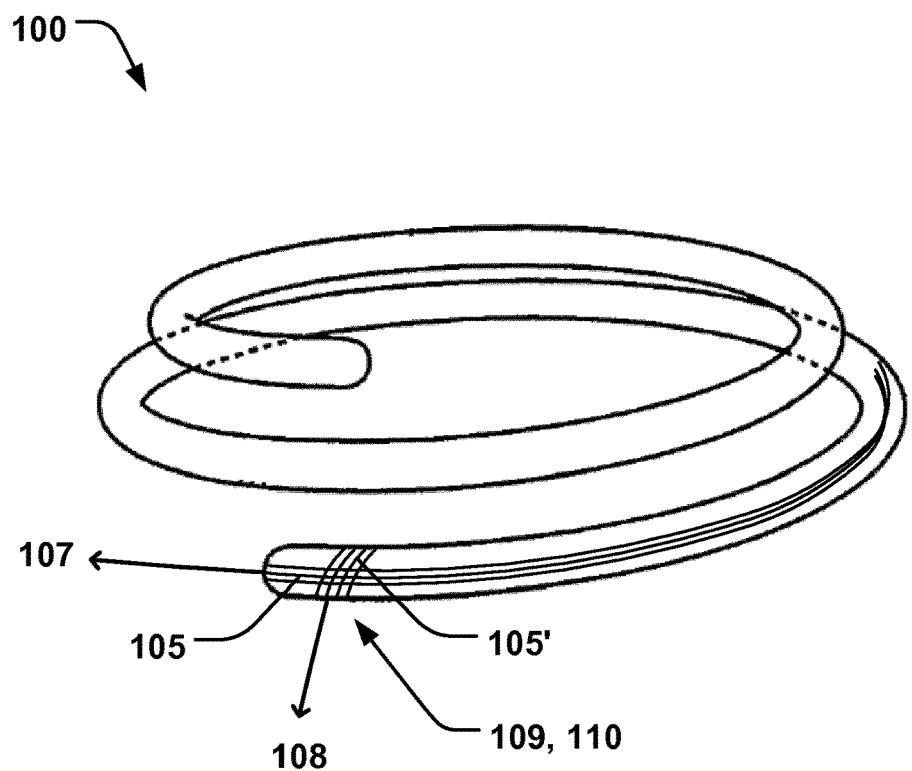
FIG. 4 is a schematic illustration of an annuloplasty implant according to one example.

The carbon fiber material 105 may comprise a weave 109 of carbon fibers, whereby a second plurality of carbon fibers 105' extends substantially in a radial direction 108 perpendicular to the longitudinal direction 107, as schematically illustrated in FIG. 4. Having a weave 109 of carbon fibers 105, 105', may provide for further improving the mechanical characteristics of the annuloplasty implant 100. For example, the stiffness of the annuloplasty implant may be increased due to the interwoven first and second plurality of carbon fibers 105, 105'. Alternatively, the second plurality of carbon fibers 105' extends substantially in the radial direction 108 without being woven with the first plurality of carbon fibers 105, as schematically illustrated in FIG. 3, i.e., providing for a layered structure of carbon fibers with a first layer of longitudinally extending carbon fibers 105, and a second layer of radially extending carbon fibers 105'. The weave 109 or layered structure of carbon fibers 105, 105', may be provided for both the first and second support rings 101 and 102, or only one of the first and second support rings 101 and 102.

The carbon fiber material 105 may comprise a tubular braid 110 of carbon fibers extending along the first and second support rings 101 and 102. The tubular form of the braid 110 may be particularly advantageous in providing structural integrity of the first and second support rings 101 and 102. The braid 110 may be formed in a layered configuration where a plurality of tubular braids are arranged concentrically within successively reduced diameters. The number of layers of tubular braids 110 may be varied to achieve desired mechanical properties of the annuloplasty implant 100 for customization to a particular application.

Figure 8A:
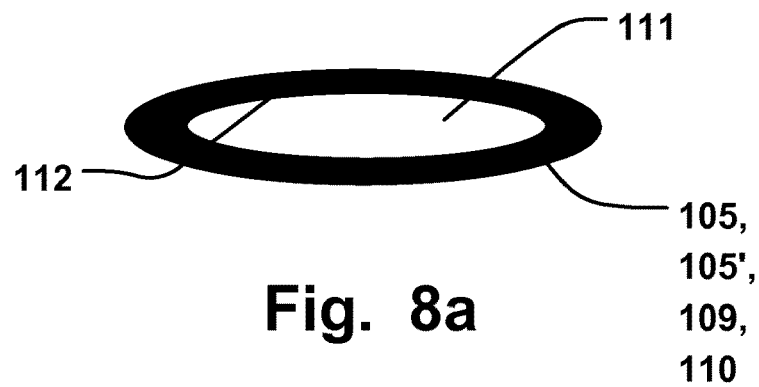
FIGS. 8a-b are schematic illustrations of cross-sections of an annuloplasty implant according to examples of the disclosure.

The first and/or second support rings 101 and 102 may comprise a core material 111 of a polymer material or metal alloy. The carbon fiber material 105 may then be at least partly arranged around a periphery 112 of the core material 111, as schematically illustrated in FIG. 8a. The carbon fiber material 105 may comprise longitudinally extending carbon fibers 105, or radially extending carbon fibers 105', or a weave 109 of carbon fibers, or a tubular braid 110 of carbon fibers. By having a core 111 of a secondary material such as a polymer material or metal alloy, the mechanical properties of the annuloplasty implant 100 can be further optimized as desired to comply with a particular application. Having a core 111 of a secondary material may for example increase the structural integrity and stiffness of the annuloplasty implant 100. The core material 111 may also be more soft and/or flexible than the carbon fiber material 105, and the carbon fiber material 105 may be used to reinforce the core 111 to achieve the desired properties. The core material 111 may have shape-memory properties, such that the first and second support rings 101 and 102 may assume an elongated configuration when delivered in a catheter, whereupon the first and second rings 101 and 102 may assume the coiled configuration when ejected from the delivery catheter. The carbon fiber material 105 may be circumferentially arranged around the periphery 112 along both first and second rings 101 and 102 or along only one of the first and second rings 101 and 102. It is also conceivable that the carbon fiber material 105 may only be arranged around only part of the periphery 112.

Figure 8B:
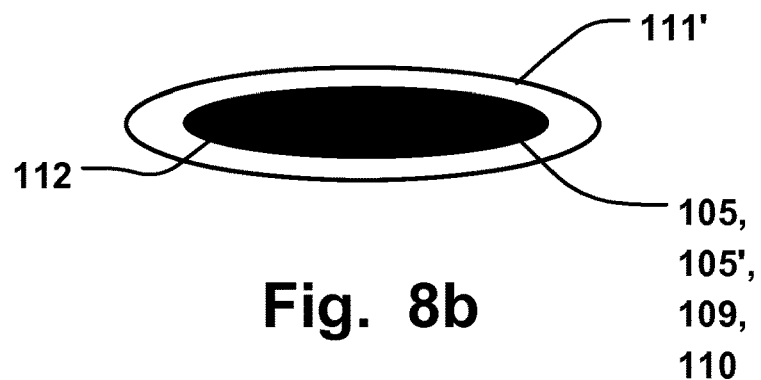

The first and/or second support rings 101 and 102 may comprise a carbon fiber core 105, 105', 109, 110, of a carbon fiber material, as illustrated in FIG. 8b. A secondary material 111' comprising a polymer material and/or a metal alloy may be at least partly arranged around a periphery 112 of the carbon core material. Thus, the carbon fiber material 105, which may comprise longitudinally extending carbon fibers 105, or radially extending carbon fibers 105', or a weave 109 of carbon fibers, or a tubular braid 110 of carbon fibers, may be configured as a supporting core 111' onto which the secondary material 111' is arranged. It is conceivable that the secondary material 111' may be a biodegradable material, which is absorbed in the body after some time, such as a temporary coating. The secondary material 111' may also be porous or otherwise configured to be penetrated by e.g. sutures or clips, such as a textile or polymer material, for fastening the annuloplasty implant 100 to the tissue. The secondary material 111' may also be configured to have a particularly low friction coefficient, such as a Teflon-like material, to facilitate delivery through a catheter. The secondary material 111' may comprise Dacron or similar materials. The secondary material 111' may also comprise a flange or collar extending radially inwards and/or outwards with respect to the center of the support rings 101 and 102 to provide for a surface that can be used for suturing the implant 100 into position, and/or provide for sealing between the implant 100 and the tissue, and/or provide for a supporting flange against the leaflets in case of extending radially inwards as mentioned.

Figure 11:
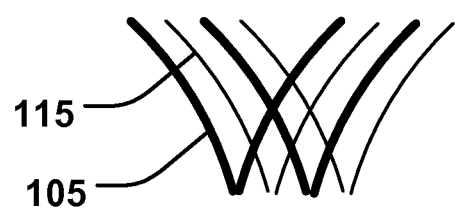
FIG. 11 is a schematic illustration of a detail of an annuloplasty implant according to one example.

The carbon fiber material 105 may be interwoven with secondary fibers 115 of a polymer material or a metal alloy, as schematically shown in FIG. 11, illustrating a section of the annuloplasty implant 100, i.e. a section of a woven part of the annuloplasty implant 100 having intertwined carbon fibers 105 and secondary fibers 115. The secondary fibers 115 may be NiTinol strands or another biocompatible material. The combination of carbon fibers 105 and a secondary material 115 may provide for advantageous properties of the annuloplasty implant 100 in terms of durability and flexibility.

Figure 5:
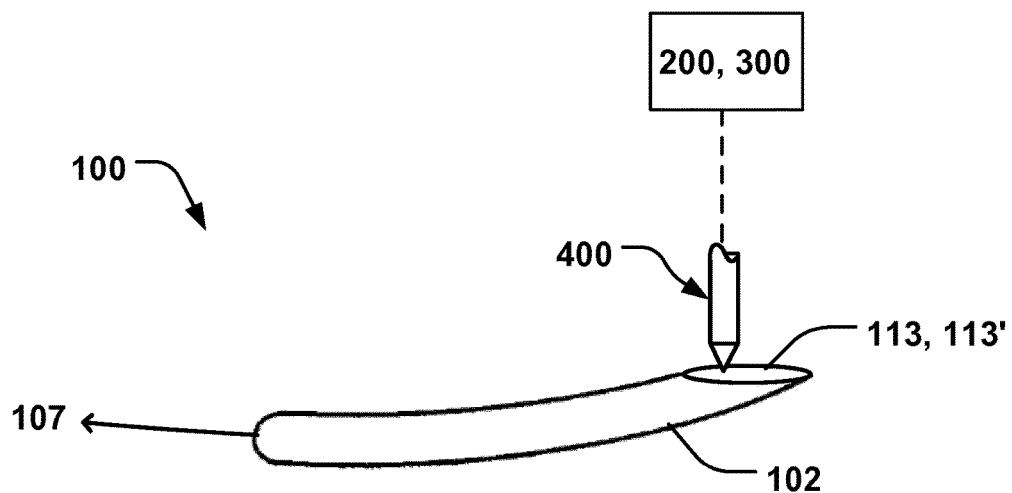
FIG. 5 is a schematic illustration of a method of manufacturing an annuloplasty implant according to one example.
Figure 6A:
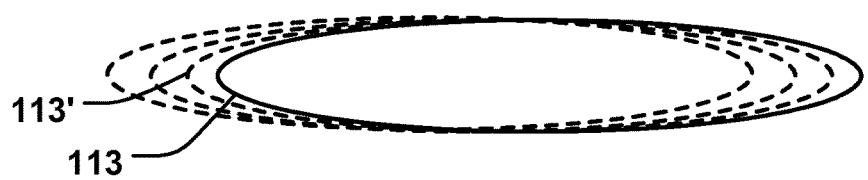
FIG. 6a is a schematic illustration of a cross-section of an annuloplasty implant according to one example.
Figure 7A:
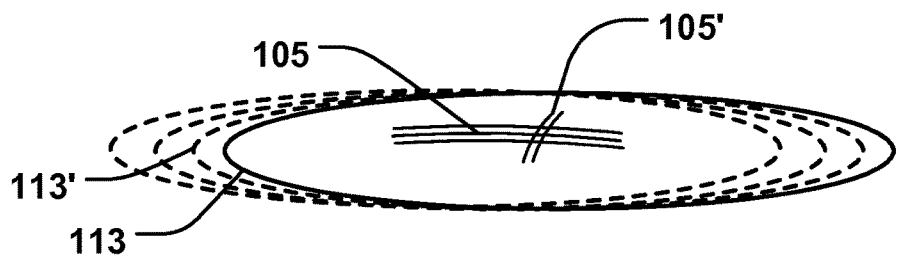
FIGS. 7a-c are schematic illustrations of cross-sections of an annuloplasty implant according to examples of the disclosure.
Figure 7B:
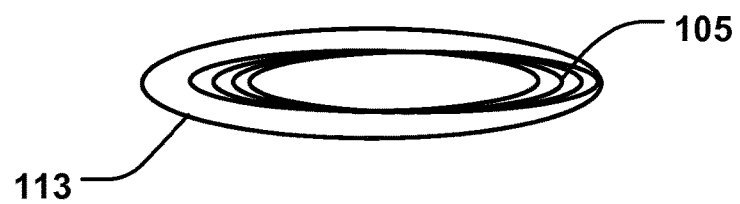
Figure 7C:
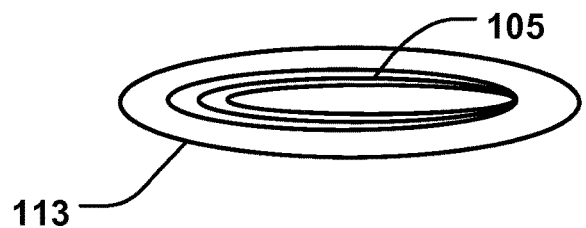

The carbon fiber material 105 may comprise a layered carbon structure formed by three-dimensional printing of a plurality of carbon layers 113, 113'. FIG. 5 schematically illustrates a three-dimensional printing process by a three-dimensional printing unit 400, depositing carbon layers 113, 113', on top of each other. The carbon layers 113, 113', are schematically illustrated in FIG. 6a, gradually building the shape of the annuloplasty ring 100. Three-dimensional printing of a layered carbon structure forming the first and second support rings 101 and 102 provides for achieving a highly customizable annuloplasty implant 100, that can be easily adapted to various anatomies and manufactured on demand. The carbon layers 113, 113', forming the annuloplasty implant 100 may be deposited and arranged in various configurations. FIG. 5 merely illustrates one example, where the cross-section of the annuloplasty implant 100, defining the periphery of each layer 113, 113', is aligned in a certain angle relative to the longitudinal direction of the support ring 102. In this case the cross-section has is relatively small compared to the longitudinal extent of the support ring 102. In the other extreme case, it is conceivable that the cross-section is aligned with an angle that is substantially parallel with the longitudinal direction 107, such that each layer 113, 113', extends along a substantial part of the longitudinal extent of the support ring 102. FIG. 7a illustrates one example where the layers 113, 113', may be formed by depositing carbon fibers 105, 105', in different orientations in the plane of the layer 113, 113'. FIG. 7a illustrates one example of depositing carbon fiber material 105 in a concentric annular pattern for forming a layer 113, whereas FIG. 7c illustrates one example where the deposition is off-set from the concentric pattern shown in FIG. 7b. These are mere examples of carbon deposition patterns and it is conceivable that the carbon fiber material 105 may be deposited in various configurations to build the layers 113, 113', of the annuloplasty implant 100.

Figure 6B:
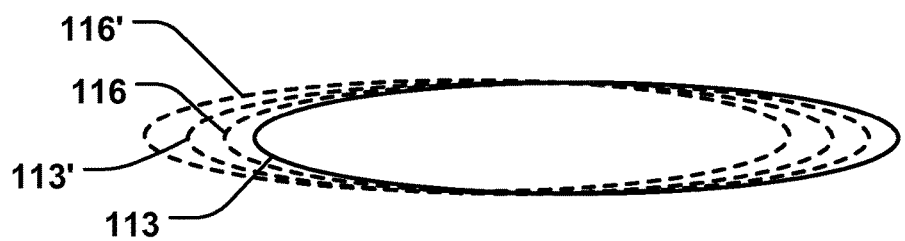
FIG. 6b is a schematic illustration of a cross-section of an annuloplasty implant according to one example.

The annuloplasty implant 100 may comprise a laminate structure having a plurality of secondary layers 116, 116', interposed between said plurality of carbon layers 113, 113', as illustrated in FIG. 6b. The laminate structure may be provided by three-dimensional printing or by other layer-depositing processes. The laminate structure may provide for improved strength of the annuloplasty implant 100 and the ability to combine advantageous characteristics of different materials for the annuloplasty implant 100. The secondary layers 116, 116', may be formed from a polymer material or a metal alloy.

Figure 10A:
FIG. 10a is a schematic illustration of an annuloplasty implant, in a side-view, according to one example.
Figure 10B:
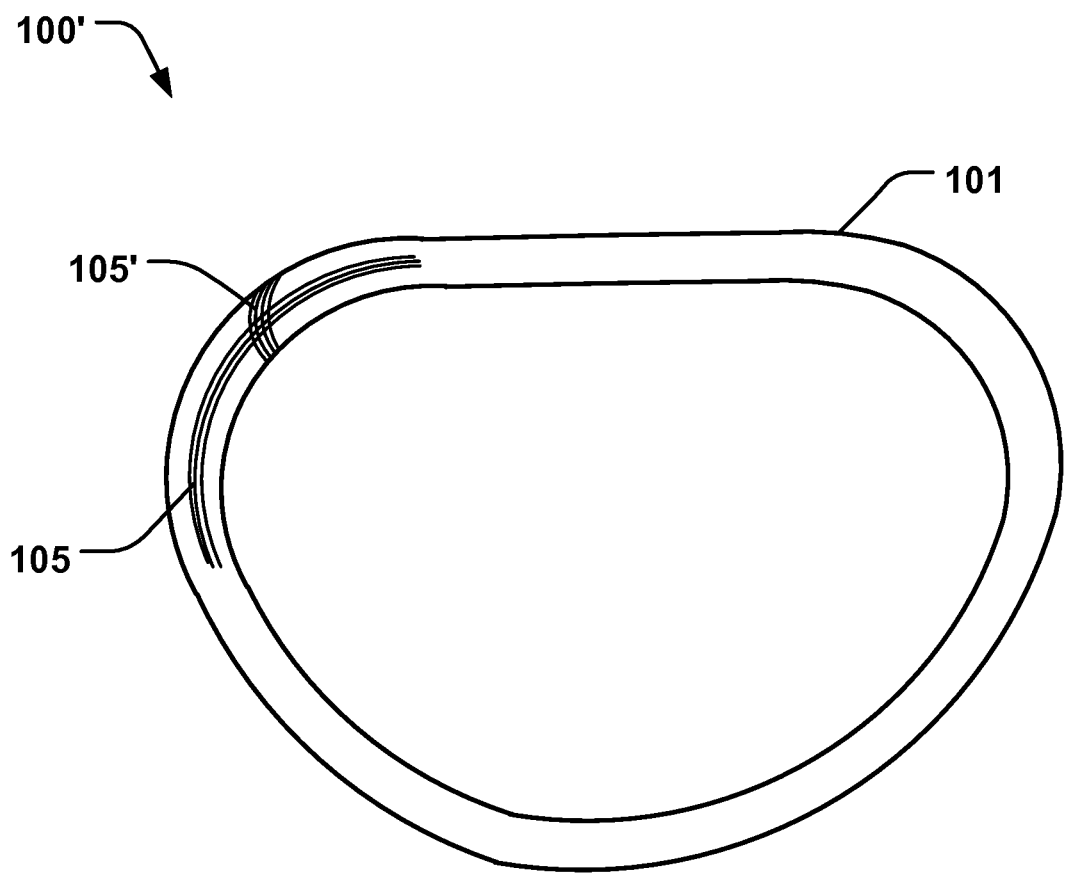
FIG. 10b is a schematic illustration of an annuloplasty implant, in a top-down view, according to one example.

Although the above annuloplasty implant 100 has primarily been described as comprising first and second support rings 101 and 102 in a coiled configuration, it is conceivable that the advantageous properties and effects provided for by the carbon fiber material 105 can also be utilized in annuloplasty rings comprising closed single-loop rings, such as D-shaped rings, or open single-loop rings, such as C-shaped annuloplasty rings. A single-loop ring 100' with a support ring 101 comprising a carbon fiber material 105 is schematically illustrated in FIGS. 10*a*-*b*, in a side-view and in a top-down view, respectively. The features described above with respect to the annuloplasty implant 100 comprising first and second support rings 101 and 102 also applies to the single loop-ring 100'. E.g. the ring 100' may comprise carbon fibers 105 arranged in the longitudinal direction, or carbon fibers 105' arranged in the radial direction, or a web 109 of carbon fibers, or a tubular braid 110 of carbon fibers, a core 111 of secondary material 100 or an outer covering 111' of secondary material, a plurality of layers 113, 113', that may be deposited by three-dimensional printing, secondary layers 116, 116', interposed between a plurality of carbon layers etc.

Figure 12:
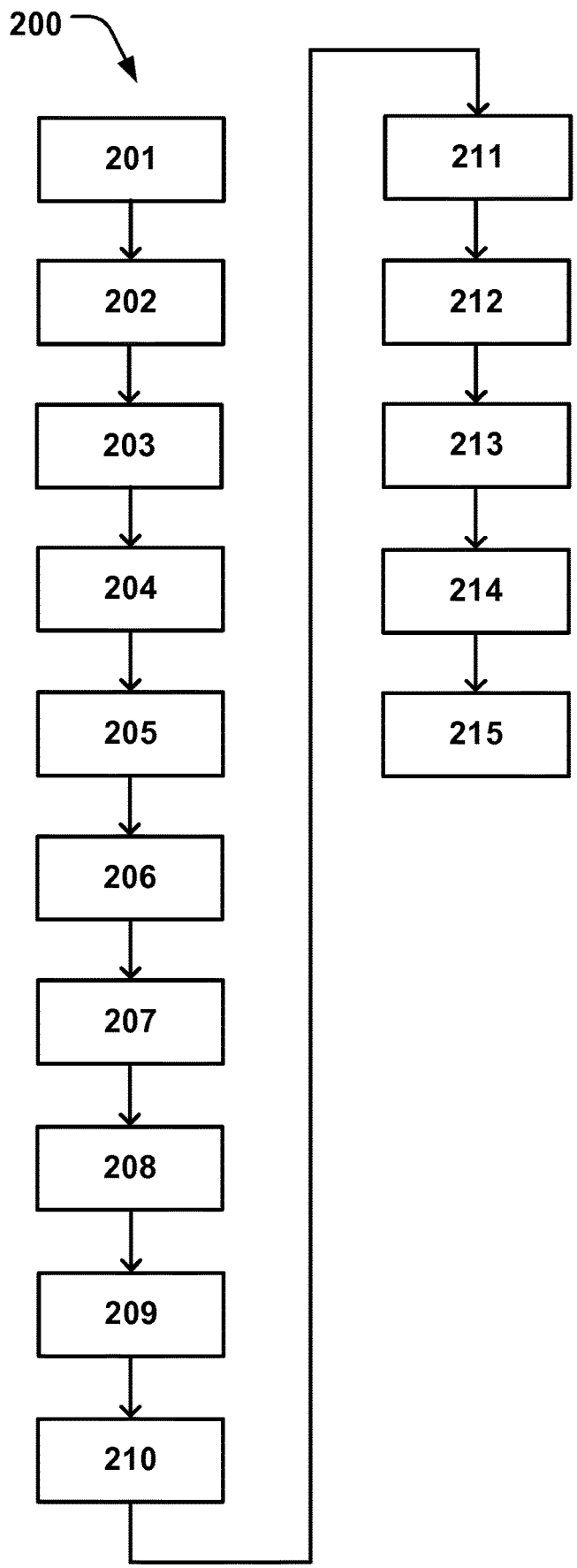
FIG. 12 is a flow chart of a method of manufacturing an annuloplasty implant according to one example.

FIG. 12 illustrates a method 200 of manufacturing an annuloplasty implant 100. The order in which the steps of the method 200 are illustrated should not be construed as limiting and it is conceivable that the order in which the steps of the method 200 is carried out may be varied. The method 200 comprises forming 201 first 101 and second 102 support rings arranged in a coiled configuration around an axial direction 103, and forming 202 at least part of said first and second support rings 101 and 102 from a carbon fiber material 105, 105'. The method 200 thus provides for an annuloplasty implant 100 with the advantageous effects described above in relation to FIGS. 1-10.

Forming the first and second support rings 101 and 102 may comprise depositing 203 material in a layer by layer deposition by three-dimensional printing, as described above. The annuloplasty implant 100 may thus be produced in an efficient and highly customizable manner, as further elucidated above. Depositing the material may comprise depositing 204 layers 113, 113', of said carbon fiber material 105, to provide for the advantageous effects described above. Depositing the material may comprise depositing 205 a secondary material 116, 116', between the layers of carbon fiber material, as described in relation to FIG. 6*b*. The secondary material 116, 116', may comprise a polymer material or a metal alloy.

The method 200 may comprise forming 206 the first and second support rings 101 and 102 of a carbon fiber core 105, 105', 109, 110, of carbon fiber material, and forming 207 a layer 111' outside said core of a secondary material, as described in relation to FIG. 8*b* above. The secondary material may be a polymer or metal alloy.

The method 200 may comprise forming 208 the first and second support rings 101 and 102 of a core 111 of a secondary material, and forming 209 a carbon fiber layer 105, 105', 109, 110, outside the core of carbon fiber material. As mentioned, the secondary material may be a polymer or metal alloy, and the carbon layer may comprise carbon fibers 105 extending longitudinally, in the longitudinal direction 107, or carbon fibers 105' extending in the radial direction 108, or a weave 109 of carbon fibers, or a tubular braiding 110 of carbon fibers.

Forming the first and second support rings 101 and 102 may comprise providing 210 an elongate portion of the carbon fiber material, and forming 211 a coiled shape having the first and second support rings 101 and 102 on a mold (not shown). The method may subsequently comprise fixating 212 the coiled shape, such as by a curing process, and removing 213 the mold.

The method 200 may comprise determining 214 dimensions of the annuloplasty implant 100 based on a three-dimensional reconstruction of a heart valve, such as a mitral valve, determined from patient medical imaging data, such as MRI- or CT-scan medical imaging data. The method 200 may then further comprise forming 215 the first and second rings 101, 102, by three-dimensional printing for patient-specific manufacturing of the annuloplasty implant 100 according to said dimensions. The method 200 thus provides for a rapid process of providing a highly customizable annuloplasty implant 100, having the benefits as elucidated above, to individual patients.

Figure 9:
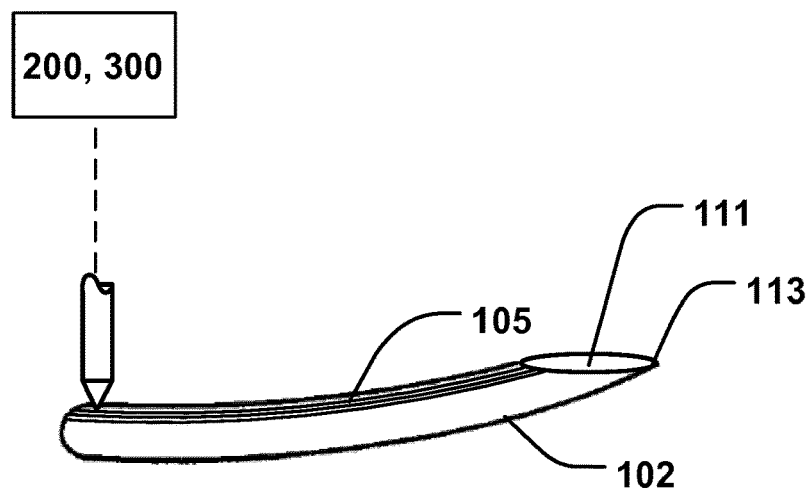
FIG. 9 is a schematic illustration of a method of manufacturing an annuloplasty implant according to one example.
Figure 13:
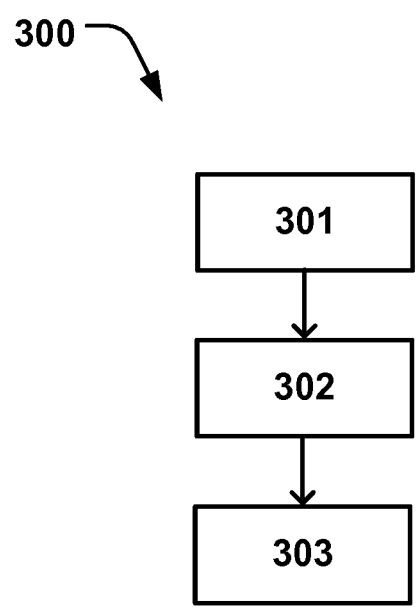
FIG. 13 is a flow chart of a method of manufacturing an annuloplasty implant according to one example.

A method 300 is thus also provided, schematically illustrated in FIG. 13, comprising determining 301 dimensions of an annuloplasty implant 100 based on a three-dimensional reconstruction of a heart valve determined from patient medical imaging data, and forming 302 first 101 and second 102 support rings arranged in a coiled configuration around an axial direction 103 by three-dimensional printing for patient-specific manufacturing of the annuloplasty implant 100 according to said dimensions. At least part of said first and second support ring 101, 102, is formed by depositing 303 a carbon fiber material 105, 105', in a layer by layer deposition by said three-dimensional printing. The advantages of having a carbon fiber material as described above can thus be provided while achieving a highly customizable method 300 of manufacturing the implant 100. FIGS. 5 and 9 are schematic illustrations of the annuloplasty implant being manufactured according to any of the methods 200 or 300.

The present invention has been described above with reference to specific embodiments. However, other embodiments than the above described are equally possible within the scope of the invention. The different features and steps of the invention may be combined in other combinations than those described. The scope of the invention is only limited by the appended patent claims.

More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used.

The invention claimed is:

1. An annuloplasty implant comprising first and second support rings arranged in a coiled configuration around an axial direction, and being adapted to be arranged on opposite sides of native heart valve leaflets to pinch said leaflets,
   wherein at least part of said first and second support ring is formed from a carbon fiber material,
   wherein said first and second support rings are resiliently movable with respect to each other in opposite directions along said axial direction, and
   wherein said carbon fiber material comprises a tubular braid of carbon fibers extending along said first and second support rings.

2. The annuloplasty implant according to claim 1, wherein said carbon fiber material further comprises a first plurality carbon fibers extending substantially in a longitudinal direction of said first and/or second support ring along an annular periphery thereof, whereby said first and second support rings are resiliently movable in perpendicular directions to said longitudinal direction of said carbon fibers.

3. The annuloplasty implant according to claim 2, wherein said carbon fiber material further comprises a weave of carbon fibers, whereby a second plurality of carbon fibers extends substantially in a radial direction perpendicular to said longitudinal direction.

4. The annuloplasty implant according to claim 1, wherein said first and/or second support ring further comprises a core material of a polymer material or metal alloy, wherein said carbon fiber material is at least partly arranged around a periphery of said core material.

5. The annuloplasty implant according to claim 1, wherein said first and/or second support ring further comprises a carbon core of a carbon fiber material, and wherein a secondary material comprising a polymer material and/or a metal alloy is at least partly arranged around a periphery of said carbon core material.

6. The annuloplasty implant according to claim 1, wherein said carbon fiber material is interwoven with secondary fibers of a polymer material or a metal alloy.

7. The annuloplasty implant according to claim 1, wherein said carbon fiber material further comprises a layered carbon structure formed by three-dimensional printing of a plurality of carbon layers.

8. The annuloplasty implant according to claim 7, further comprising a laminate structure having a plurality of secondary layers interposed between said plurality of carbon layers.

9. The annuloplasty implant according to claim 1, wherein said first and second support rings are configured to assume an elongated configuration when delivered in a delivery catheter and assume said coiled configuration to pinch said leaflets when ejected from the delivery catheter.

* * * * *